United States Patent [19]

Garcia

[11] Patent Number: 4,962,769
[45] Date of Patent: Oct. 16, 1990

[54] USE OF BUBBLE PACKAGING FILM FOR RELIEVING DECUBITUS ULCERS OR PRESSURE ULCERS

[75] Inventor: Mario C. Garcia, West St. Paul, Minn.

[73] Assignee: Prevent Products, Inc., St. Louis Park, Minn.

[21] Appl. No.: 326,087

[22] Filed: Mar. 20, 1989

Related U.S. Application Data

[63] Continuation-in-part of Ser. No. 192,531, May 11, 1988, abandoned.

[51] Int. Cl.$^5$ ............................................. A61F 13/00
[52] U.S. Cl. ................................................... 128/889
[58] Field of Search ...................... 5/341, 432, 449, 41; 128/60, 889, 68; 623/36; 604/397

[56] References Cited

U.S. PATENT DOCUMENTS

| | | | |
|---|---|---|---|
| 2,777,440 | 1/1957 | Baker | 5/431 |
| 3,459,179 | 8/1969 | Olesen | 128/60 |
| 3,480,280 | 11/1969 | Gamertsfelder | 5/449 |
| 3,608,961 | 9/1971 | Heck | 128/68 |
| 3,762,404 | 10/1973 | Sakita | 5/449 |
| 3,828,785 | 8/1974 | Gamm et al. | 604/397 |
| 3,886,939 | 6/1975 | Boxer | 128/60 |
| 3,968,530 | 7/1976 | Dyson | 5/449 |
| 4,067,330 | 1/1978 | Roache | 128/889 |
| 4,233,966 | 11/1980 | Takahashi | 128/60 |
| 4,813,405 | 3/1989 | Filip | 128/60 |

Primary Examiner—Robert A. Hafer
Assistant Examiner—Charles H. Sam
Attorney, Agent, or Firm—Haugen and Nikolai

[57] ABSTRACT

Body fluid absorbing cushioning means for use by invalids and bed-ridden persons for absorption of body waste fluids and for relief of pressure areas on the skin. The cushioning means comprises a laminate with at least three layers including an inner water absorbent layer, an outer generally water impervious layer, and a center layer consisting of an array of generally closely spaced enclosures defining air supported closed cells. Further, in order to accommodate transfer of body fluids from the inner layer, bores may be formed in the center layer between individual enclosures, wherein a second water absorbing layer is provided on the opposite side of the impervious cell layer.

11 Claims, 3 Drawing Sheets

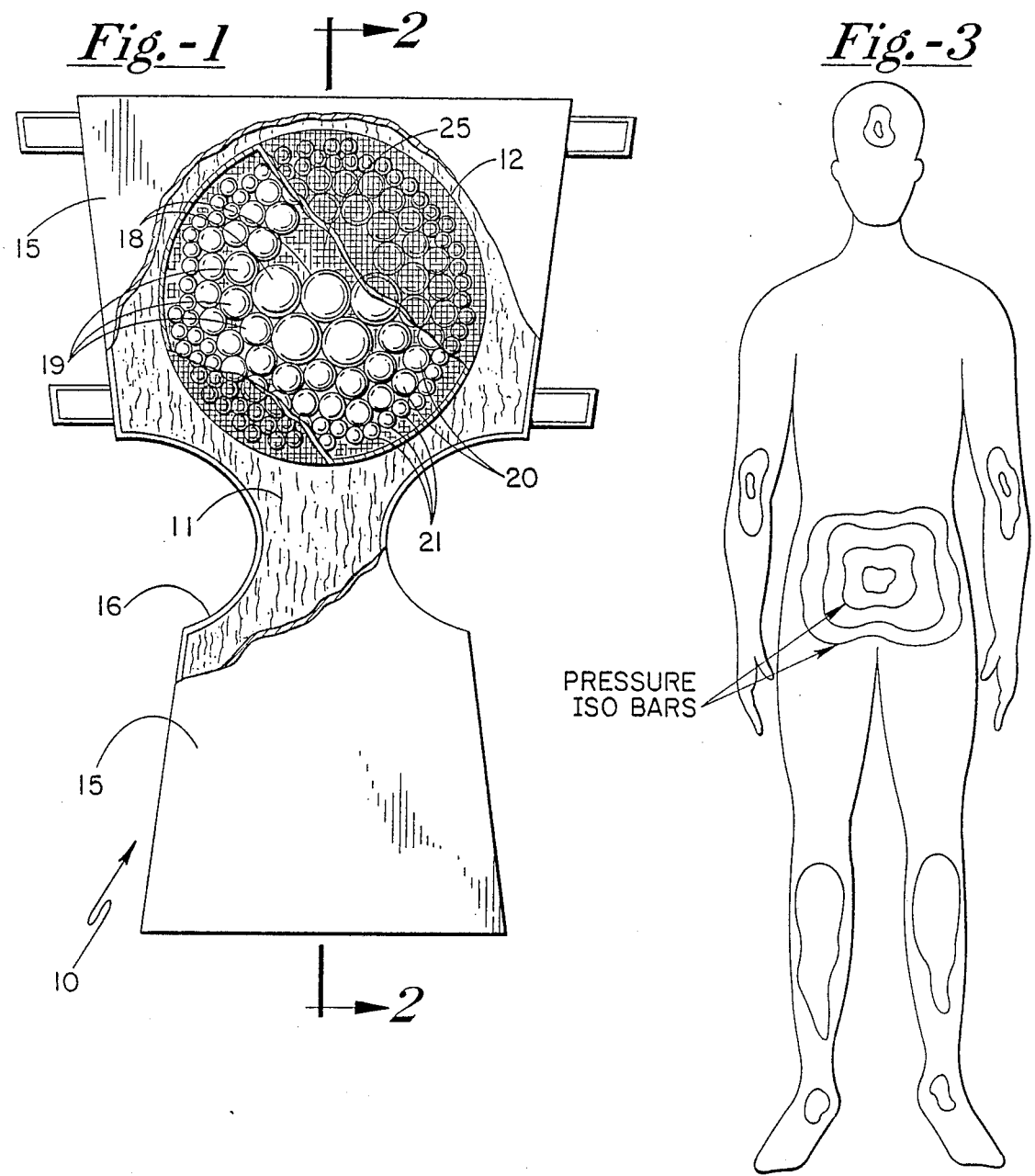
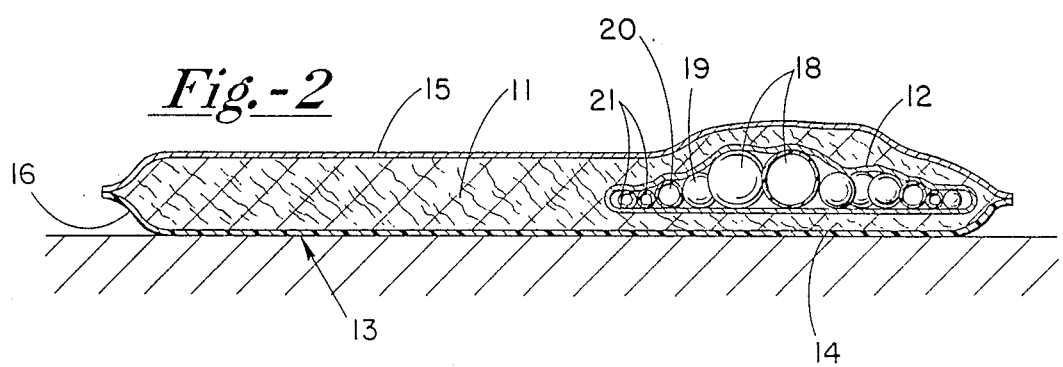

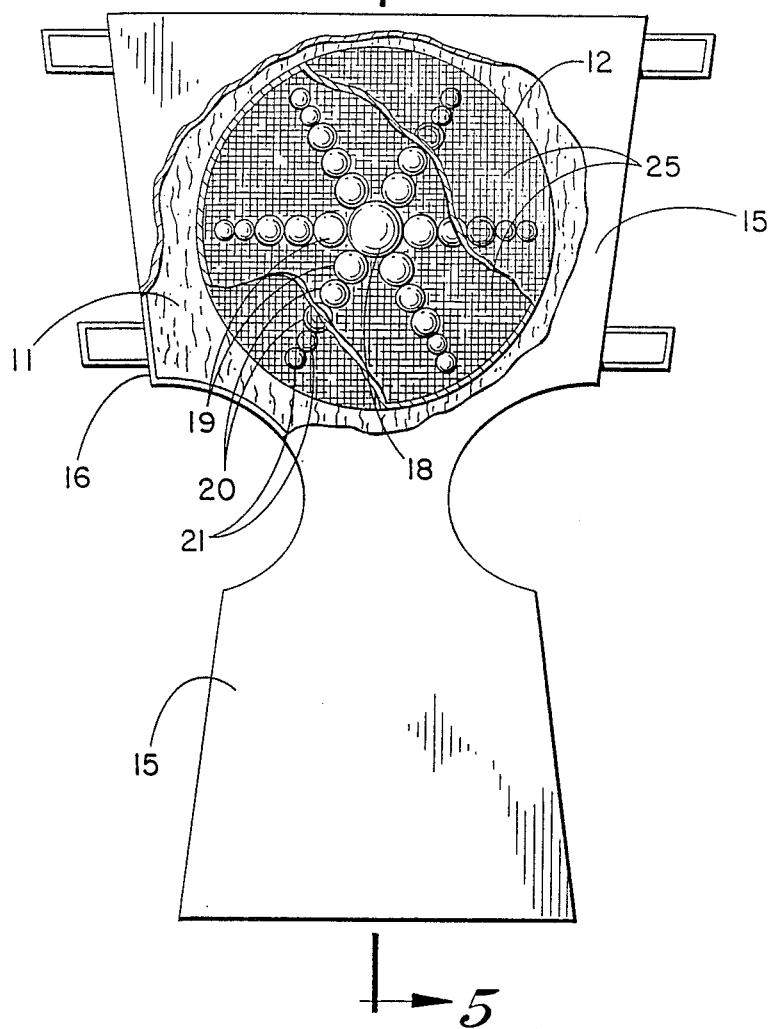
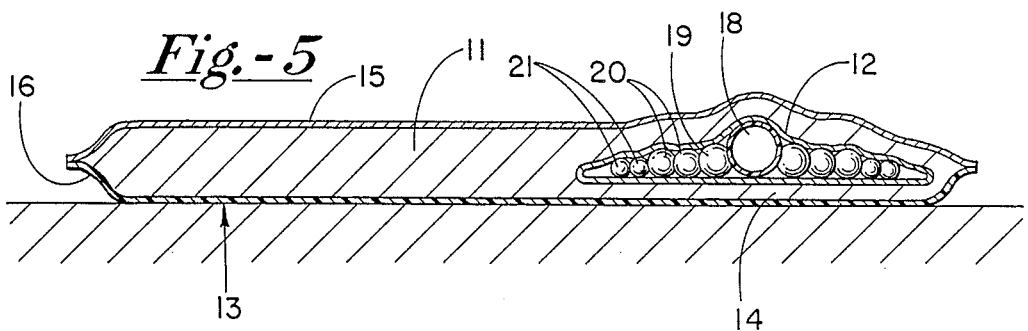

USE OF BUBBLE PACKAGING FILM FOR RELIEVING DECUBITUS ULCERS OR PRESSURE ULCERS

CROSS-REFERENCE TO RELATED APPLICATION

The present application is a continuation-in-part of my co-pending application Ser. No. 07/192,531, filed May 11, 1988 and entitled "USE OF BUBBLE PACKAGING FILM FOR RELIEVING DECUBITUS ULCERS OR PRESSURE ULCERS", now abandoned.

BACKGROUND OF THE INVENTION

The present invention relates generally to cushioning means for use by invalids, bed-ridden persons, as well as others who may be required to spend extended periods of time in either a sitting or prone position, and more specifically to body fluid absorbing cushioning means which are adapted to control and/or reduce the unit pressures exerted against the skin of such persons while so confined. The present invention is adapted primarily for reduction of the occurrence of decubitus ulcers, commonly known as bed sores, which frequently develop on the surface of skin of invalids and persons who may be bed-ridden or otherwise required to remain in a given position over extended periods of time, without being able to change positions on their own.

Normally, humans are supported by surfaces such as chairs and/or beds, and the bodies press against the skin surface with a total force generally equal to the body weight. Pressure, which may be defined as force per unit area, is exerted on the body surface over various ranges, depending upon the location, the physiology of the person, as well as the nature of the supporting surface. These pressures frequently become substantial at certain localized areas, but may be reduced when the body is floated in water or upon other cushioning means. While higher pressures can be tolerated by most individuals for short periods of time, extended exposures to high pressures at certain localized areas of the skin and/or body will eventually lead to skin necrosis and/or tissue anoxia.

The creation of decubitus ulcers or "bed sores" is an example of skin necrosis. When the blood supply to the skin is obstructed due to application of continuous pressures over extended periods of time, skin necrosis occurs, and a decubitus ulcer or bed sore may develop. Interruption of blood flow from the subcutaneous tissue over periods in excess of a few hours will generally lead to such conditions.

One way of decreasing unit pressures is to avoid concentration of forces upon limited areas. Normally, when a healthy adult male is lying supine on a bed, his total weight is substantially equally distributed across 180 square inches of body area, with the average pressure on the body surface being about 0.8 psi or 40 mm Hg. However, in practice, the weight is not equally distributed on the skin surface, but depends upon body orientation, as well as the disposition of subcutaneous bony structures or the like. In the past, work undertaken by Lindau, Greenway, and Piazza in 1965 mapped out pressure distribution on the body surface. In the accompanying drawings, FIG. 3 shows the results for the pressure distribution on a healthy adult male lying supine, with each isobar representing a constant pressure zone or area. High pressure areas are normally concentrated in the buttocks and heel for the supine position, this being the position normally assumed or occupied by bed-ridden persons.

Sitting positions result in a somewhat modified form of pressure distribution, with the highest pressure being over the ischial tuberosities and the thigh area. Typically, most of the bed sores on the bodies of wheelchair or bed-ridden patients are found around the hips where three predominant sites occur, these being the coccyx region, the trochanter of the femur, and the ischial. These areas represent, respectively, 43%, 12% and 9% of the occurrences of such ulcers and/or sores.

SUMMARY OF THE INVENTION

In accordance with the present invention, pressure points on the body are reduced through the use of a means for improved distribution of pressure. Specifically, a plastic sheet, preferably perforated, utilizing closely spaced air sacs or bubbles is employed. Generally, since bed-ridden patients are sometimes incontinent, a laminate is provided with at least three layers including an inner water absorbent layer, an outer generally water impervious layer, and a center area consisting of an array of generally closely spaced enclosures defining air supported closed cells with each cell defining an enclosed spaced of predetermined volume. The array of cells includes a number of cells with varying diameters, wherein cells of larger diametrical size are disposed where forces are greater, so as to further reduce the creation of high unit pressures within the cells. Bores and/or ports are arranged in the zones between individual cells so as to provide, when desired, a means for body fluid transmission to a second water absorbing layer situated on the opposed side of the impervious cell layer.

Therefore, it is a primary object of the present invention to provide an improved fluid absorbing cushioning means for use by invalids and bed-ridden persons for reduction of occurrences of decubitus ulcers, along with improved absorption of body waste fluids, thus providing for relief of pressure areas on the skin of such persons.

It is yet a further object of the present invention to provide an improved body fluid absorbing cushioning means which comprises a laminate with at least three layers including an inner water absorbent layer, an outer generally water impervious layer, and a center layer consisting of an array of generally closely spaced enclosures defining air supported closed cells of predetermined size and volume, and with the individual cells being arranged in an array with the center cells of relatively large diameter, and radially outwardly positioned cells being of relatively reduced diameter, thus further avoiding the creation of local areas of high unit pressures.

Other and further objects of the present invention will become apparent to those skilled in the art upon a study of the following specification, appended claims, and accompanying drawing.

IN THE DRAWING

FIG. 1 is a top plan view of a body fluid absorbing cushioning means prepared in accordance with the present invention, and with portions of the inner water absorbent layer being removed so as to expose the center layer;

FIG. 2 is a vertical sectional view taken along the line and in the direction of the arrows 2—2 of FIG. 1;

FIG. 3 is a comparison of pressure distribution in a healthy adult male, with zones of equal pressure being connected by isobars on specific areas of the skin surface;

FIG. 4 is a plan view similar to FIG. 1, and illustrating a modified form of the present invention;

FIG. 5 is a vertical sectional view taken along the line and in the direction of the arrows 5—5 of FIG. 4, and further illustrating the embodiment of FIG. 4.

DESCRIPTION OF THE PREFERRED EMBODIMENT

Figure 6:
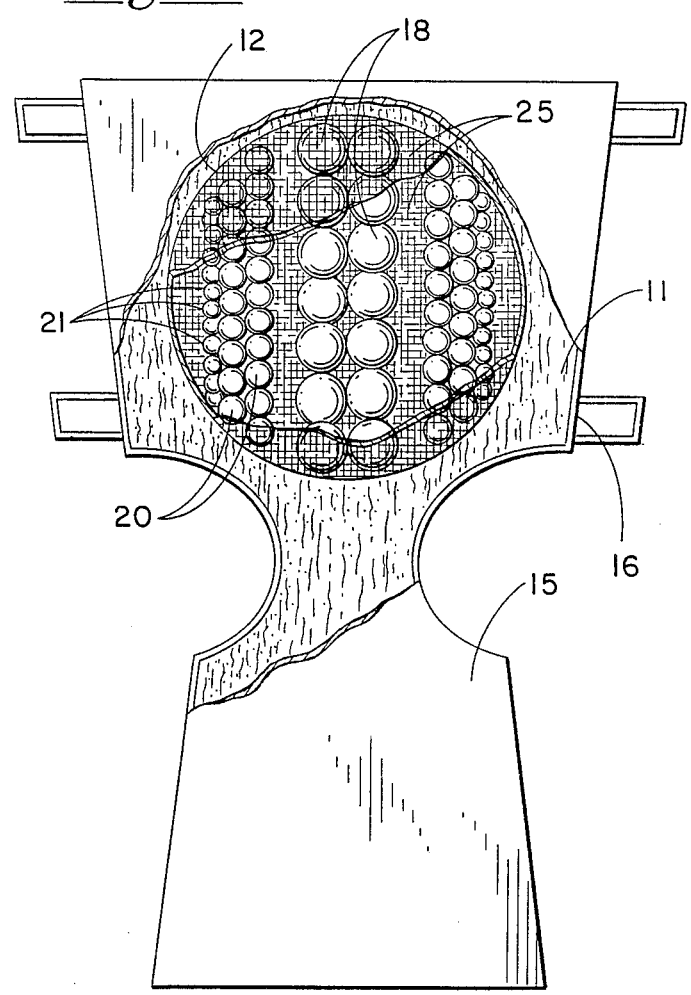
FIG. 6 is a plan view of a modified form of device utilizing a system with laterally spaced arrays of differing size.

With specific attention being directed to FIGS. 1 and 2 of the drawing, the body fluid absorbing cushioning means generally designated 10 includes a laminate structure with at least three layers, including an inner water absorbent layer 11, a center layer 12 consisting of an array of generally closely spaced enclosures defining air supported closed cells, and an outer generally water impervious layer 13. For certain applications, a second water absorbent layer 14 may be provided on the other side of the cell layer from water absorbent layer 11. A water pervious outer layer may be provided as at 15, along with a water impervious layer as at 16.

The individual cells forming layer 12 include an array of generally closely spaced enclosures defining air supported closed cells. Each cell defines an enclosed air space of predetermined volume. In the arrangement illustrated in FIGS. 1 and 2, descending diametrical sizes of cells are provided, as at 18, 19, 20 and 21. Specifically, the system preferably employs four separate sizes, with the larger size range being in the center as illustrated at 18, with the first reduced size being shown at 19. The diameters of the cells at 19 are generally on a ratio of 0.82:1 with respect to the larger centrally located cells 18. Additionally, cells in the array as at 20 have a size or diameter ratio of approximately 0.58:1 with respect to the centrally located large cells 18. The smallest cells in the array are at the outer portion of the circle, and generally have a diameter ratio of 0.41:1 with respect to the larger centrally located cells 18. With attention now being directed to FIGS. 4 and 5 of the drawing, wherein such a modified form of the invention is illustrated. Specifically, in the embodiment of FIGS. 4 and 5, a pattern is arranged with voids being formed in the cell array, as illustrated at 25. Specifically, a number of the cells in this area are removed in order to reduce pressure on the area of the skin covering the coccyx, and thus further reduce the creation of force concentration leading to high unit pressures.

In still a further modified configuration, openings may be formed in the array so as to provide direct support on the areas surrounding the coccyx, trochanter and ischium. In these arrangements, support is provided in the openings and/or areas immediately surrounding these normal high pressure points.

Arrays of individual cells of the type employed in connection with the present invention are generally known, with such arrays of cells being employed in the packing business. These arrays generally comprise thermally bonded films of polyethylene, polypropylene or the like.

In certain applications and modifications, it may be desirable to provide an array of cells wherein a rectangular or "X-Y" arrays are provided. Such systems are, of course, deemed equivalent to the circular arrays, and those cells disposed outwardly from the center will, of course, have a somewhat smaller diameter, in the ranges or ratios set forth hereinabove. Also, it will be appreciated that variations in these ratios may be utilized as well. Such an array will, of course, tend to reduce the unit pressures achieved in the centrally located cells, while achieving some uniformity with pressures in the outwardly disposed cells.

As a still further embodiment of the present invention, the features and advantages may be found present in this arrangement. Specifically, the bubble size is designed to remain constant while the density of the individual bubbles diminishes from a central point outwardly. Such an arrangement may be made on an X-Y coordinate basis in the form of rows and columns, or in a radially arranged array. The lower density is achieved through greater inter-bubble spacing.

In accordance with the modification illustrated in FIG. 6, the absorbent layer 11 utilizes a discrete bubble or cell array as shown at 12', with the large cell centered along the elongated axis as at 18', and with smaller cells being illustrated at 20'—20' and 21'—21'. A lateral space as shown at 25' is provided between adjacent rows of bubbles or cells. The device shown in FIG. 6 further includes panels 15' and 16', as is common with all embodiments.

With continued attention being directed to FIG. 6, it will be observed that the three individual strips of discrete bubble or cell arrays are spaced apart, with the lateral spacing being shown at 25'. This lateral spacing provides a drainage zone to permit urine or other body fluids to pass through the bubble area and into the more highly absorbant cellulose padding or material. In other words, the spacing or gaps 25' will serve as holes or access zones for the urine to pass through to the absorbant material.

The advantage of this configuration is that three individual strips of stock bubble or cell arrays may be used in order to render it capable of producing the material on a substantially continuous or roll basis.

As indicated in connection with the embodiments of FIGS. 1-5, it is, of course, contemplated that drainage areas for permitting urine and/or other body fluids to pass through to the absorbant cellulose material, bores may be formed between individual bubbles, or in certain instances, in lieu of an individual discrete bubble. For convenience, the individual openings may be in the area of approximately one-quarter inch diameter, with the individual openings being spaced on an X-Y axes at one-inch centers. Individual punches may be used on a continuous basis in order to accommodate substantially continuous production.

Other and further embodiments of the present invention may become apparent to those skilled in the art.

What is claimed is:

1. Body fluid absorbing cushioning means for use by invalids and bed-ridden persons for absorption of body waste fluids and for relief of pressure areas on the skin of such persons, said fluid absorbing cushioning means comprising:

(a) a laminate with at least three layers including an inner water absorbent layer, an outer generally water impervious layer, and a center layer consisting of a fixed geometrical array of abutting enclosures defining air supported closed cells with each cell defining an enclosed space of predetermined volume;

(b) said fixed array including individual cells of said array of varying thickness and being disposed so as to reduce concentration of pressure forces upon predetermined areas of the body and skin surrounding the coccyx, trochanter and ischium areas of the body, and to transfer certain of the load from said predetermined areas to areas where bodily loading is normally lower than in said predetermined areas.

2. The body fluid absorbing cushioning means as defined in claim 1 being particularly characterized in that individual cells within said array are generally circular, and with varying diameters, and wherein cells of larger size are disposed where forces are greater so as to reduce the creation of high unit pressures within said cells.

3. The body fluid absorbing cushioning means as defined in claim 2 wherein the cell sizes of greater diameter are disposed in the zone covering the coccyx, trochanter and ischium areas of the body.

4. The body fluid absorbing cushioning means as defined in claim 1 being particularly characterized in that said cells are arranged in a pattern with voids arranged therealong, and wherein said closed cells are removed from the areas covering the coccyx, trochanter and ischium.

5. The body fluid absorbing cushioning means as defined in claim 1 being particularly characterized in that individual cells in said array are arranged in a generally circular pattern extending outwardly from a central locus, and with the cell size decreasing with an increase in radial spacing from said central locus.

6. The body fluid absorbing cushioning means as defined in claim 1 being particularly characterized in that cell sizes are arranged with at least four different diameters.

7. The body fluid absorbing cushioning means as defined in claim 6 being particularly characterized in that the ratio of cell diameters from larger to smaller is generally in the range of 80%, 60%, and 40% of the largest diameter.

8. The body fluid absorbing cushioning means as defined in claim 6 being particularly characterized in that said cell sizes, from larger to smaller, are in the range of 1:1, 0.82:1; 0.58:1; and 0.41:1.

9. The body fluid absorbing cushioning means as defined in claim being particularly characterized in that water absorbing layers are disposed on either side of said impervious cell layer, and wherein the cells are spaced apart, one from another, and wherein the space between said cells is perforated so as to permit water absorption from the inner water absorbing layer through said cell layer and into said outer water absorbing layer.

10. The body fluid absorbing cushioning means as defined in claim 1 being particularly characterized in that said array of generally closely spaced enclosures comprises laterally spaced apart discrete groups of such enclosures and wherein cells of a larger size are disposed generally along the central axis of said body fluid absorbing cushioning means, and wherein cells of substantially smaller sizes are in said laterally disposed groups of cells.

11. The body fluid absorbing cushioning means as defined in claim 9 being particularly characterized in that said array of generally closely spaced enclosures comprises laterally spaced apart discrete groups of such enclosures and wherein cells of a larger size are disposed generally along the central axis of said body fluid absorbing cushioning means, and wherein cells of substantially smaller sizes are in said laterally disposed groups of cells.

* * * * *

UNITED STATES PATENT AND TRADEMARK OFFICE
CERTIFICATE OF CORRECTION

PATENT NO. : 4,962,769

DATED : October 16, 1990

INVENTOR(S) : Mario C. Garcia

It is certified that error appears in the above-identified patent and that said Letters Patent is hereby corrected as shown below:

Column 6, line 13, "claim being" should read -- Claim 1 being --.

Signed and Sealed this

Fourteenth Day of January, 1992

Attest:

HARRY F. MANBECK, JR.

*Attesting Officer*  *Commissioner of Patents and Trademarks*